(12) United States Patent
Gupta et al.

(10) Patent No.: US 11,622,731 B2
(45) Date of Patent: Apr. 11, 2023

(54) METHOD AND SYSTEM FOR DETECTING AN EVENT AND DETERMINE INFORMATION ABOUT IT (LIKE ITS STRENGTH) USING RESISTIVE STATE CHANGES OF A MEMRISTOR

(71) Applicant: UNIVERSITY OF SOUTHAMPTON, Southampton (GB)

(72) Inventors: Isha Gupta, Southampton (GB); Alexantrou Serb, Southampton (GB); Themistoklis Prodromakis, Southampton (GB)

(73) Assignee: UNIVERSITY OF SOUTHAMPTON, Southampton (GB)

( * ) Notice: Subject to any disclaimer, the term of this patent is extended or adjusted under 35 U.S.C. 154(b) by 142 days.

(21) Appl. No.: 16/342,072

(22) PCT Filed: Oct. 16, 2017

(86) PCT No.: PCT/GB2017/053120
§ 371 (c)(1),
(2) Date: Apr. 15, 2019

(87) PCT Pub. No.: WO2018/073566
PCT Pub. Date: Apr. 26, 2018

(65) Prior Publication Data
US 2019/0246993 A1  Aug. 15, 2019

(30) Foreign Application Priority Data

Oct. 18, 2016  (GB) ...................................... 1617631

(51) Int. Cl.
*A61B 5/00*  (2006.01)
*G11C 13/00*  (2006.01)
(Continued)

(52) U.S. Cl.
CPC .............. *A61B 5/7282* (2013.01); *A61B 5/24* (2021.01); *A61B 5/40* (2013.01); *A61B 5/6877* (2013.01);
(Continued)

(58) Field of Classification Search
CPC ........... A61B 5/24; A61B 5/40; A61B 5/4064; A61B 5/6877; A61B 5/7282;
(Continued)

(56) References Cited

U.S. PATENT DOCUMENTS 5,913,076 A * 6/1999 Yamada .................... G06F 3/05
710/69
6,873,282 B1 * 3/2005 Murphy ................ G04F 10/005
341/164
(Continued)

FOREIGN PATENT DOCUMENTS

WO    2017001956 A1    1/2017

OTHER PUBLICATIONS

Baranauskas, "What Limits the Performance of Current Invasive Brain Machine Interfaces," Frontiers in Systems Neuroscience, vol. 8, Article 68, pp. 1-10 (Jan. 2014).
(Continued)

*Primary Examiner* — Patrick Fernandes
*Assistant Examiner* — Anna Roberts
(74) *Attorney, Agent, or Firm* — Volpe Koenig

(57) ABSTRACT

The present invention provides a method and system for processing data from an event, such as a neurological event. When a neurological event occurs, a spike in a neural waveform is generated. The spike can be detected and used to determine information about the neurological event. The method uses data values from a resistive switching component capable of undergoing a resistive state change when a voltage is applied to it. The data values represent a sequence
(Continued)

of resistive state changes of the resistive switching component which correspond to the neurological event. The method further comprises processing the received data values to identify a resistive state change corresponding to the neurological event and to obtain information about the neurological event. Thus, a method and system for processing neural spikes is provided.

32 Claims, 4 Drawing Sheets

(51) Int. Cl.
    G11C 27/00      (2006.01)
    G06N 3/063      (2006.01)
    G06N 3/04       (2006.01)
    A61B 5/24       (2021.01)
    G06N 3/049      (2023.01)

(52) U.S. Cl.
    CPC .......... *G06N 3/049* (2013.01); *G06N 3/0635* (2013.01); *G11C 13/004* (2013.01); *G11C 13/0007* (2013.01); *G11C 27/00* (2013.01); *A61B 2562/0285* (2013.01); *G11C 2013/0054* (2013.01)

(58) Field of Classification Search
    CPC .......... A61B 2562/0285; G06N 3/049; G06N 3/0635; G11C 13/004; G11C 13/0007; G11C 27/00; G11C 2013/0054
    See application file for complete search history.

(56) References Cited

U.S. PATENT DOCUMENTS

| | | | | |
|---|---|---|---|---|
| 8,749,422 | B1* | 6/2014 | Moore ................ | H03M 1/1215 341/155 |
| 9,466,364 | B1 | 10/2016 | Papandreou et al. | |
| 9,721,661 | B1* | 8/2017 | Buchanan .............. | G11C 15/04 |
| 10,593,403 | B2* | 3/2020 | Buchanan ............ | G11C 13/003 |
| 2009/0292661 | A1* | 11/2009 | Haas ..................... | G06N 3/0635 706/33 |
| 2010/0299297 | A1 | 11/2010 | Breitwisch et al. | |
| 2012/0011092 | A1* | 1/2012 | Tang ...................... | G06N 3/063 706/33 |

OTHER PUBLICATIONS

Berdan et al., "Emulating Short-Term Synaptic Dynamics with Memristive Devices," Scientific Reports, pp. 1-9 (2016).
Brown et al., "Multiple Neural Spike Train Data Analysis: State-of-the-Art and Future Challenges," Nature Neuroscience, vol. 7, No. 5, pp. 456-461 (May 2004).
Eversmann et al., "A 128 x 128 CMOS Biosensor Array for Extracellular Recording of Neural Activity," IEEE Journal of Solid-State Circuits, vol. 38, No. 12, pp. 2306-2317 (Dec. 2003).
Frey et al., "Microelectronic System for High-Resolution Mapping of Extracellular Electric Fields Applied to Brain Slices," Biosensors & Bioelectronics, vol. 24, No. 7, pp. 2191-2198 (Mar. 2009).
Gupta et al., "A Cell Classifier for RRAM Process Development," IEEE Transactions on Circuits and Systems II: Express Briefs, vol. 62, No. 7, pp. 676-680 (2015).
Gupta et al., "Improving Detection Accuracy of Memristor-Based Bio-Signal Sensing Platform," IEEE Transactions on Biomedical Circuits and Systems, pp. 203-211 (2016).
Gupta et al., "Memristive Integrative Sensors for Neuronal Activity," arXiv preprint arXiv: 1507.06832 (2015).
Gupta et al., "Practical Operation Considerations for Memristive Integrating Sensors," 2016 IEEE International Symposium on Circuits and Systems, pp. 2322-2325 (May 2016).
Gupta et al., "Real-Time Encoding and Compression of Neuronal Spokes by Metal-Oxide Memristors," Nature Communications, (No. 7), Article 12805 (Sep. 2016).
Gupta et al., "Sub 100 nW Volatile Nano-Metal-Oxide Memristor as Synaptic-Like Encoder of Neuronal Spikes," IEEE Transactions on Biomedical Circuits and Systems, pp. 351-359 (2018).
Gupta et al., "Supplementary Information: Real-time Encoding and Compression of Neuronal Spokes by Metal-Oxide Memristors," pp. 1-10 (Sep. 2016).
Gupta et al., "Towards a Memristor-Based Spike-Sorting Platform," 2016 Biomedical Circuits and Systems Conference, pp. 408-411 (Oct. 2016).
Hierlemann et al., "Growing Cells Atop Microelectronic Chips: Interfacing Electrogenic Cells In Vitro with CMOS-based Microelectrode Arrays," Proceedings of the IEEE, vol. 99, No. 2, pp. 252-284 (Feb. 2011).
Jeong et al., "Emerging Memories: Resistive Switching Mechanisms and Current Status," Reports on Progress in Physics, vol. 75, No. 7 (Jul. 2012).
Lewicki, "A Review of Methods for Spike Sorting: the Detection and Classification of Neural Action Potentials," Network: Computation in Neural Systems, vol. 9, pp. R53-R78 (1998).
Lopez et al., "A 966-Electrode Neural Probe with 384 Configurable Channels in 0.13 μm SOI CMOS," IEEE Transactions on Biomedical Circuits and Systems, vol. 11, No. 3, pp. 510-522 (206).
Marblestone et al., "Physical Principles for Scalable Neural Recording," Frontiers in Compartive Neuroscience, vol. 7, p. 1-39 (2013).
Nicolas-Alonso et al., "Brain Computer Interfaces, a Review," Sensors, vol. 12, No. 2, pp. 1211-1279 (Jan. 2012).
Paraskevopoulou et al., "A Sub-1μW Neural Spike-Peak Detection and Spike-Count Rate Encoding Circuit," IEEE Biomedical Circuits and Systems Conference, pp. 29-32 (Nov. 2011).
Prodromakis et al., "Two Centuries of Memristors," Nature Materials, vol. 11, No. 6, pp. 478-481 (Jun. 2012).
Rey et al., "Past, Present, and Future of Spike Sorting Techniques," Brain Research Bulletin, vol. 119, pp. 10-117 (Apr. 2015).
Serb et al., "Live Demonslialion: A Versatile, Low-Cost Platform for Testing Large ReRAM Cross-Bar Arrays," IEEE International Symposium on Circuits and Systems, vol. 9, No. 5 (2014).
Massimiliano Di Ventra et al: "Circuit elements with memory: memristors, memcapacitors and meminductors", Arxiv.org, Cornell University Library, 201 Olin Library Cornell University Ithaca NY 14853, Jan. 23, 2009 (Jan. 23, 2009), XP080358607 DOI: 10.1109/JPROC.2009.2021077.

* cited by examiner (b)

METHOD AND SYSTEM FOR DETECTING AN EVENT AND DETERMINE INFORMATION ABOUT IT (LIKE ITS STRENGTH) USING RESISTIVE STATE CHANGES OF A MEMRISTOR

The present invention relates to analysis of data from neurological measurements.

Rapid development in neuroscience has led to development of standard tools in neuroscience research capable of acquiring long-term, extra-cellular neural activity [1], [2]. These advances permit recording biological signals, e.g. neurological signals, using micro-electrodes, with state-of-art technology capable of simultaneously recording the biological signals from up-to thousands of sites in-vivo [3] or by employing 32k site Complementary-Metal-Oxide-Semiconductor (CMOS) based platform in-vitro offering sub-cellular resolution [2]. The resulting, enormous amount of multi-channel data generated (which can be Gb/s) imposes severe limitations on power consumption [4] and the bandwidth required for wireless transmission [5], which is being addressed by tremendous efforts in the area of on-chip spike-detection [6]. When a neurological event occurs, a spike in a neural waveform/signal is generated. The spike can be detected and used to determine information about the neurological event. However, one of the major impediments in neuroscience research is providing the capability to analyse the large quantity of information which needs to be processed from the large ensemble of neurons. This is majorly limited by the computational resources required for sorting the acquired data [7]. The complexity of spike-sorting algorithms remains as one of the major bottlenecks in emerging neuroprosthetic applications (e.g. brain-computer interfaces) [6], [8]-[10].

Recently, a neural activity detector, for neuroprosthetic applications that does not require precise, individual spike-timing resolution was proposed [11]. This system exploits the intrinsic properties of a novel component named a 'memristor', which can concurrently act as both storage and computation element [12], [13], and which is an example of a resistive switching component. The memristor can be a fully back-end integrable nanoscale device which can change its memory state (i.e. its resistive state) as a function of the integral of the input voltage applied across the memristor, when the stimulus (i.e. the input voltage) exceeds the intrinsic switching threshold of the device, thus behaving as 'noise-suppressing' integrating sensors. It has been previously shown that memristor devices generally encode spiking activity in gradual, non-volatile resistive state changes, which means the state of the device no longer needs to be read in real-time. The resistive state of the device is assessed periodically at an application-specific sampling rate (i.e. sampling rate is traded-off for timing resolution). The presence/absence of activity (i.e. resistive state changes) in distinct time bins reveals the number of spikes detected by the proposed 'Memristive Integrating Sensor (MIS)' platform, thus successfully operating as a 'spike-detector' [11].

It is an object of the invention to improve analysis of data obtained from neurological measurements.

According to an aspect of the invention, there is provided a method for processing data from a sensor, comprising: receiving data values representing a sequence of resistive state changes of a resistive switching component resulting from applying an output from at least one sensor to the resistive switching component, wherein the resistive switching component is capable of undergoing a resistive state change when a voltage above a threshold voltage is applied across the resistive switching component; and processing the received data values to identify a resistive state change corresponding to an event and to obtain information about the event other than temporal information from the resistive state change.

According to an alternative aspect of the invention, there is provided a system for processing data from a sensor, comprising a processor configured to: receive data values representing a sequence of resistive state changes of a resistive switching component resulting from applying the output from at least one sensor to the resistive switching component, wherein the resistive switching component is capable of undergoing a resistive state change when a voltage above a threshold value is applied across the resistive switching component; and process the received data to identify a resistive state change corresponding to an event and to obtain information about the event other than temporal information from the resistive state change.

The invention will be more clearly understood from the following description, given by way of example only, with reference to the accompanying drawings, in which:

FIG. 1 depicts a system for processing data from an event in accordance with an embodiment;

FIG. 2a depicts an output from a sensor, wherein the output has a voltage which varies over time, and FIG. 2b depicts the resulting change of resistance of a resistive switching component wherein the output of FIG. 2a is applied across the resistive switching components and different gains are applied to the output from the sensor so that the maximum voltage within in the output was mapped from −1V to −6V in different cases;

Figure 1:
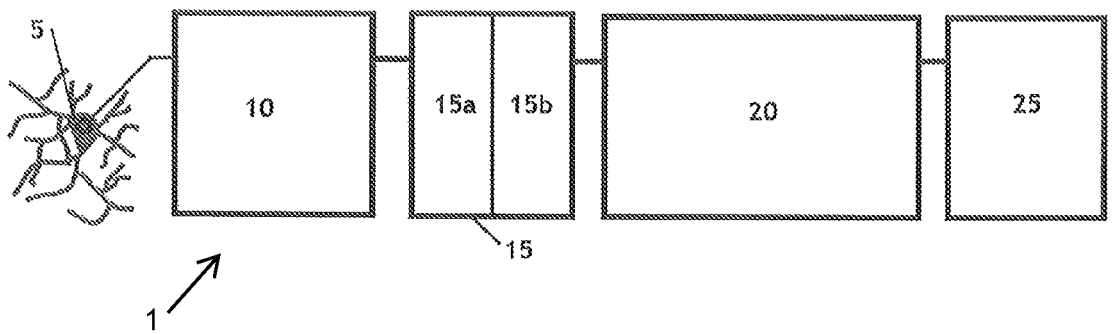
Figure 5A:
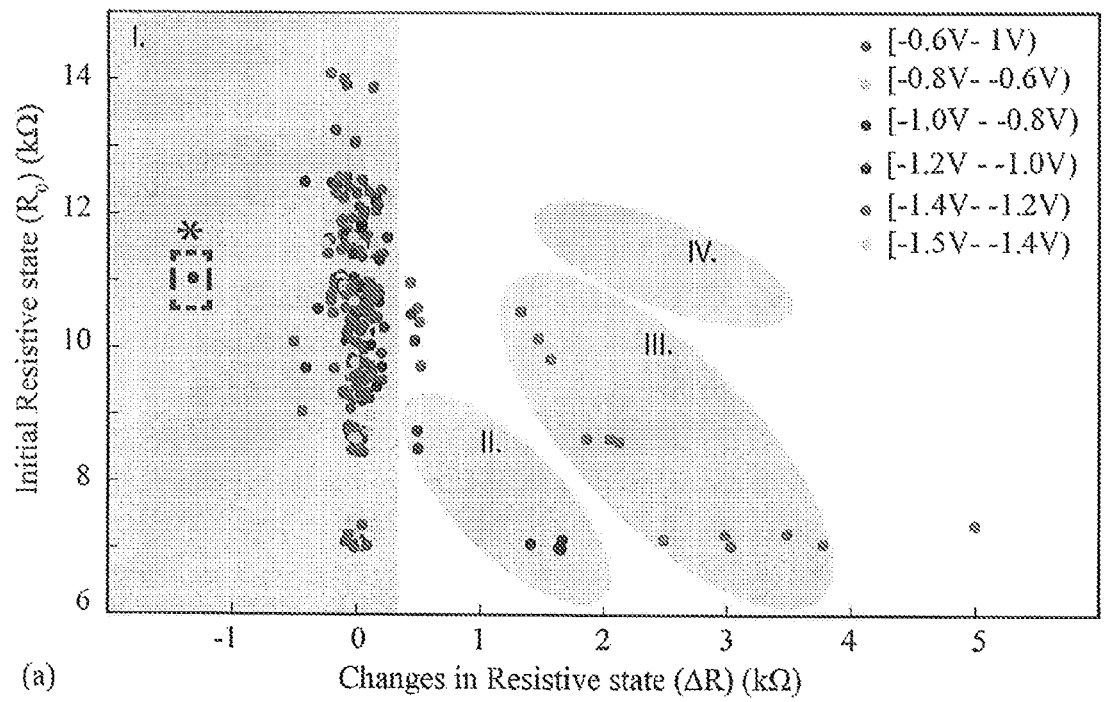
Figure 5B:
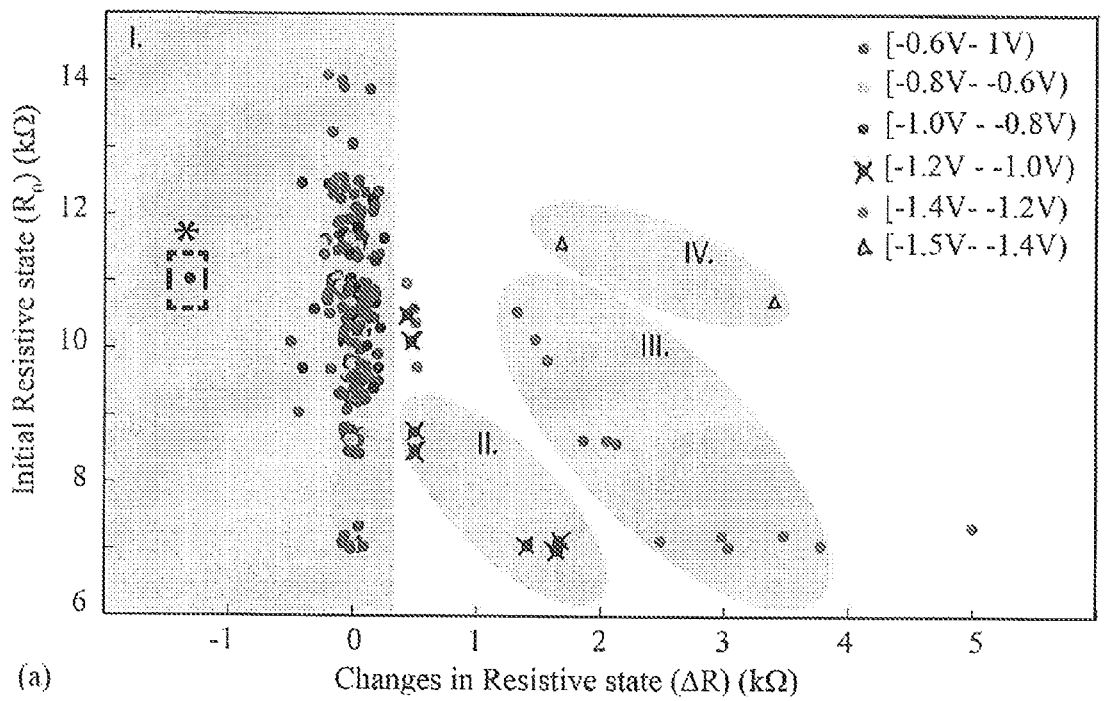
Figure 5C:
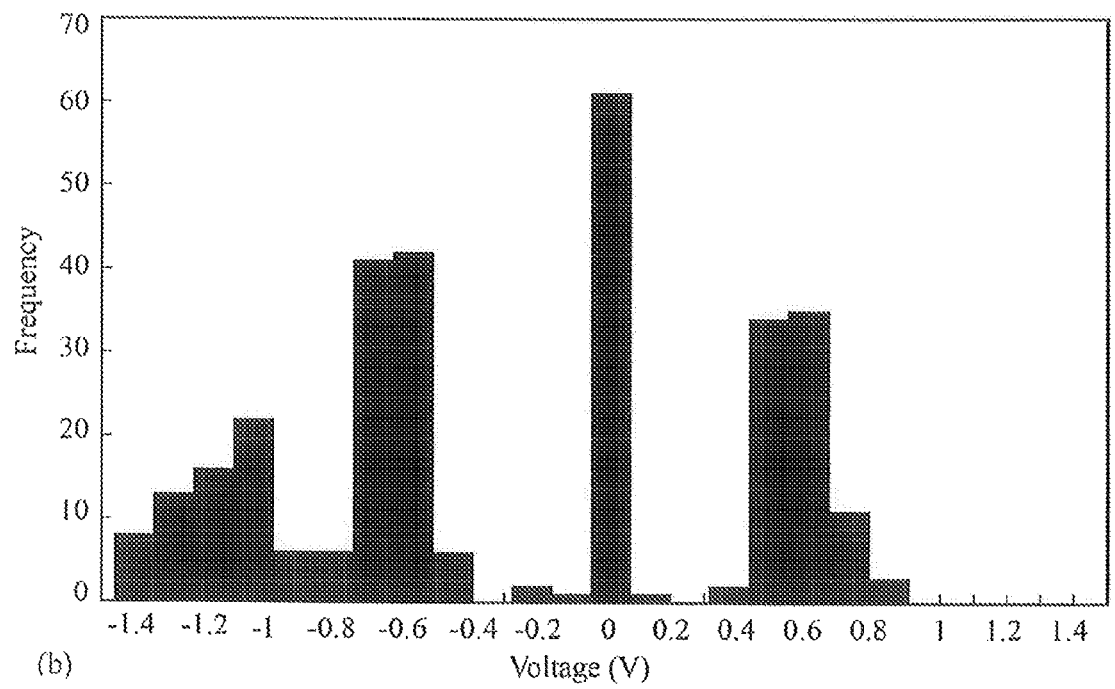
Figure 6:
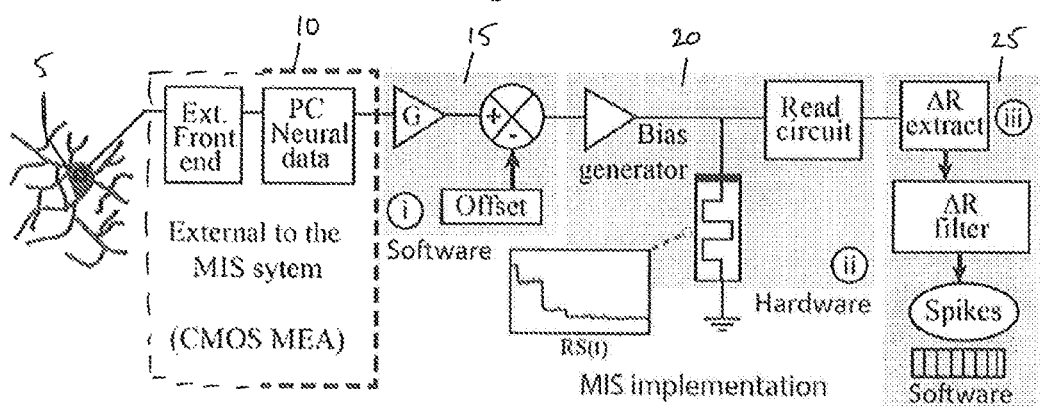

FIG. 5a depicts a scatter plot for the initial resistive state vs changes in resistive state of a resistive switching component, FIG. 5b depicts the graph of FIG. 5a wherein points above the threshold have been distinguished from one another, and FIG. 5c depicts a frequency histogram for maximum voltages within each bin of data, corresponding to the data values representing the events shown in FIG. 5a and FIG. 5b; and FIG. 6 depicts the system of FIG. 1 with additional details included.

The same references are used for similar features throughout the drawings. The features shown in the figures are not necessarily to scale and the size or arrangements depicted are not limiting. It will be understood that the figures may include optional features which are not essential to any embodiments. Furthermore, not all of the features are depicted in each figure and the figures may only show a few of the components relevant for a describing a particular feature.

The prospects of spike-sorting from the power-efficient MIS elements are discussed and described in further detail below. A neurological sensor may be used to measure neural waveforms being generated by at least one neuron. Since the neural waveform is transduced in the memory state changes of the memristive devices (i.e. the resistive state changes of resistive switching components), the number of characteristics that can be exploited for spike-sorting is limited.

However, the richness of the input neural waveform being analysed is preserved in the resistive state changes of the device-under-test (DUT), i.e. the resistive switching component. The resistive state changes are sensitive to both 'amplitude' and 'polarity' of the neural waveform and are thus sensitive to both amplitude and polarity of biased events such as neurological events which result in a spike. The inventors have recognised that the effect of these two parameters on the resistive state changes of the DUT, i.e. the relevant resistive switching component, can be analysed and it is possible to arrive at important conclusions based on this analysis.

In an embodiment, a method is provided for processing data from a sensor. The method comprises receiving data values representing a sequence of resistive state changes of a resistive switching component resulting from applying an output from at least one sensor to the resistive switching component. The resistive switching component is capable of undergoing a resistive state change when a voltage above a threshold voltage is applied across the resistive switching component. The method further comprises processing the received data values to identify a resistive state change corresponding to an event and obtaining information about the event other than temporal information from the resistive state change.

Known methods for processing certain types of event, such as neurological events are limited in the information they can provide. In particular, it is known to process a neural waveform to obtain the timing of neurological events, e.g. the time at which a neurological event occurs. The change in resistive state may be represented by a portion of the data values. The data values may represent the changes in the resistive state of the resistive switching component over fixed intervals of time. The change in resistive state may correlate to when a neurological event occurs, i.e. the change in resistive state may be due to a spike in the neural waveform. From measuring and analysing the neural waveform, and detecting resistive state changes represented by the data values, temporal information such as the frequency of the neurological events and/or the time at which a neurological event occurs may be determined. Due to the issues described above in relation to the large quantity of data acquired which is not easily processed, it is normal to determine temporal information relating to the neurological event only. However, in the present embodiment, other characteristics may also be determined, such as the location of the neurological event, the size or intensity of the neurological event (as determined by a weighted integral of the output of the sensor typically dominated by the maximum amplitude), etc.

The method may be implemented using electronic-based implementation. In other words, the method may be computer-implemented. This may include using software, hardware and/or firmware to implement the method. Additionally or alternatively, this may include using an integrated circuit and/or a printed circuit board and/or any other appropriate electronic circuit structure.

The event may be any type of event which relates to a waveform (i.e. a signal) of an appropriate form. Thus, if the waveform is a voltage/current series over time, then events may be indicated by a change in the waveform which can be detected by a sensor. The event may be a biological event. For example, the event may be a neurological event. An example of a neurological event may be a firing of a neuron. The spike in the neural waveform during a neurological event may be caused by an action potential being generated by a neuron, which results in a sharp deviation from the baseline of the neural waveform. It may be particularly beneficial to determine certain characteristics relating to the neurological event, such as the location. The location of the neurological event equates to the location of the neuron which generates the neurological event. In other words, the method may comprise determining the "address" of the source neuron, indicating the neuron which generates the neurological event. The event may be referred to as a neurological event from hereon in, however, it is understood that data relating to other types of event may be processed instead.

The method of obtaining information about a neurological event uses data values which are representative of the neurological event. An exemplary system 1 for carrying out the method is depicted in FIG. 1. As shown, a neurological sensor 10 may be used to take measurements of a neuron 5. Thus, the neurological sensor may measure the neural waveform at a particular location. The neurological sensor may pick up variations due to multiple neurons. The neural waveform thus indicates neurological events by spikes in the neural waveform relating to multiple neurons. The neurological sensor 10 outputs an electrical output. The output may be sent to an optional voltage modifying device 15 to boost the voltage of the output from the neurological sensor 10. The output has a variation of voltage over time. A resistive switching component 20 may be provided which undergoes changes in resistive state in response to the voltage of the output applied across it. For further details of a resistive switching component, please see "Real-time encoding and compression of neuronal spikes by metal-oxide memristors" by Isha Gupta, Alexantrou Serb, Ali Khiat, Ralk Zeitler, Stefano Vassanelli and Themistoklis Prodromakis, Nature Communications (ncomms12805). The resistive switching component 20 provides corresponding data values. The data values represent the change of resistive state of the resistive switching component. The data values may be received by a processor 25 which is configured to process the data values.

The sensor may be any sensor capable of detecting waveforms described above and capable of detecting events in the waveform. For example, if the data being processed relates to a neurological event, the sensor may be a neurological sensor. In other words, the type of sensor will depend on the type of event about which information is being obtained. The sensor may be referred to as a neurological sensor from hereon in, however, it is understood that the sensor type may vary depending on the waveform being detected and/or measured.

The neurological sensor 10 may be configured and used, as depicted in FIG. 1, to detect and measure neurological changes. Thus, the method may comprise the step of measuring neurological events, or more particularly, of measuring a neural waveform which has neurological events. The neurological sensor 10 may be used in various ways, for example, in vitro or in vivo. The neurological sensor 10 may store measurements at the neurological sensor 10. Alternatively, the measurements may be passed in real time (or with minor delay) to the resistive switching component 20 or may be stored in another device which can send the measurements to the resistive switching component 20 at a desired time.

The output from the neurological sensor 10 is normally an electrical output which has a voltage. The voltage of the output varies over time. The voltage of the output varies depending on the neural waveform, and spikes in the neural waveform lead to corresponding spikes in the voltage of the output. Thus there are large, sharp increases in the voltage of the output when a neurological event occurs.

When the voltage is applied across the resistive switching component 20, the resistance of the resistive switching component 20 changes. Thus, the resistance of the resistive switching component 20 may result from applying the output from at least one neurological sensor 10 across the resistive switching component 20. The resistance of the resistive switching component 20 varies over time due to the varying input voltage (of the output of the neurological sensor 10 which may optionally have passed through a voltage modifying device 15). The output of the neurological sensor 10 may be considered as the input to the resistive switching component 20.

As will be described in further detail below, the resistive switching component 20 may undergo a resistive state change when a voltage above a threshold voltage is applied across it. A resistive state change is indicated by a sharp change in the resistance of the resistive switching component 20, as depicted in FIG. 3b. Large changes in resistance may correspond to resistive state changes.

A sequence of resistive state changes may occur as a result of the voltage variation applied to the resistive switching component 20 over time. Not all changes in resistance are a resistive state change, however, a resistive state change does include a change in resistance. The resistive state change may comprise a change in resistance at a constant temperature, or a substantially constant temperature. A change in resistance does not necessarily equate to a change in resistive state. Small variations in the neural waveform would not likely lead to a change in the output which would alter the resistive state of the resistive switching component 20. However, changes that are large enough will lead to resistive state changes. This can be seen in FIG. 3b.

The resistive switching component 20 may otherwise be referred to as a memristor or memristor device. The dominant device behavioural feature of the resistive switching component 20 may be the memristance of the component, i.e. the ability of the resistive switching component 20 to retain, even for a short time, the variation of resistance of the component. Various devices may be considered as a resistive switching component 20. For example, RRAM, FeRAM, STTRAM, PCMRAM and others are different forms or technological implementations of components exhibiting resistive switching. For convenience, these devices may be referred to as memristors, or resistive switching components.

The change of resistance, and thus the resistive state changes, may be retained by the resistive switching component 20 for a predetermined amount of time. The change of resistance (and the resistive state changes) may be retained by the resistive switching component 20 for a sufficient amount of time to allow for the detection and measurement of the resistive state changes. The amount of time may only be long enough to allow detection and measurement. The amount of time may be as low as a few hundred microseconds. The amount to time may be at least approximately 0.1 ms, or at least approximately 1 ms or more. There is no particular upper limit and the amount of time could even go up to ten years or even more. The amount of time required will depend on the specific implementation of the method and the operating parameters selected by the user.

The resistive switching component 20 may comprise non-volatile resistive state transition. This means that the resistive switching component 20 may retain the change of resistance (and thus the resistive state changes) until the resistance of the resistive switching component 20 is reset. Thus, the amount of time may be set depending on the time needed to carry out the required measurements, i.e. the resistive switching component 20 may be controlled to define the amount of time for which the resistive state changes are retained.

As described, the resistive switching component 20 may undergo a resistive state change when a voltage above a threshold voltage is applied across the resistive switching component 20. More generally, the resistance of the resistive switching component 20 may not change enough to cause a resistive state change when the voltage is below a threshold voltage. An example of the output from the neurological sensor 10 is depicted in FIGS. 2a and 3a. The output clearly shows spikes in the voltage which may correlate to a neurological event. However, the voltage of the output needs to be large enough to register a change in the resistance of the resistive switching component 20.

The voltage threshold value may otherwise be referred to as the intrinsic switching threshold, and is the voltage below which the output will not change the resistive state of the resistive switching component. The resistive switching component 20 may therefore be considered to be noise supressing because it may not register a change when the voltage applied across the resistive switching component 20 is below a threshold voltage. If the voltage is below the threshold voltage, then the resistive state of the resistive switching component 20 will not necessarily be changed, meaning that the resistive switching component 20 may not adequately respond to the output from the neurological sensor 10. Thus, there may not be a resistive change unless the voltage is greater than the threshold voltage. This is indicated in FIG. 2b, which shows the resistance change in response to the output depicted in FIG. 2a. In FIG. 2b the greyed out area indicates the initial resistive state range of the resistive switching device 20 before the output is applied. After the output (at different gains) is applied, if the resistance of the resistive switching component 20 is in the grey band, then the maximum voltage in the output was below the threshold voltage value. This threshold indicated in FIG. 2b is exemplary only and may be different for different components.

In order to increase the voltage above the threshold voltage value, a gain and/or an offset may be applied to the output from the neurological sensor 10 such that the voltage is over the threshold voltage value. The method may comprise amplifying the output from the neurological sensor 10. Additionally or alternatively, the method may comprise applying a voltage offset to the output from the neurological sensor 10. The output may be amplified and/or offset using a voltage modifying device 15 as depicted in FIG. 1. The voltage modifying device 15 may comprise an amplifying portion 15a (equivalent to an amplifier) and/or an offsetting portion 15b (equivalent to an offsetting device). The amplifying portion 15a and the offsetting portion 15b may be provided integrally with one another in one device. The gain and/or the offset applied to the output should be selected carefully. The resistance of the resistive switching component 20 should change enough to have a resistive state change in response to variations such as spikes in the neural waveform which may correlate to a neurological event.

Different gains may be applied to the output of the neurological sensor 10 to increase the voltage over the threshold value using the amplifying portion 15a of the voltage modifying device 15. FIG. 2b shows a variation of gain voltages having been applied to the output from the neurological sensor 10 depicted in FIG. 2a such that the maximum voltage of the output was mapped from −1V to −6V for the different gains. FIG. 2b shows the change of resistance of the resistive switching component 20 over time. As shown in the graph in FIG. 2b, when the gain results in a maximum voltage between −1V to −3V, the resistance of the resistive switching component 20 is mostly in the grey region indicating that the maximum voltage in the output was below the threshold voltage value. However, a gain which results in a maximum voltage of −4V to −6V could be used to adapt the output from the neurological sensor 10 such that the change in resistance in the resistive switching component 20 can result in resistive state changes which can be processed to obtain information about the neural waveform.

The offset may be used to counter possible asymmetries in the input waveform or in the response of the resistive switching component 20 itself (the positive and negative thresholds are not necessarily of similar magnitudes). The voltage modifying device 15 may use the offsetting portion 15b to apply an offset to the output from the neurological sensor 10 which may for example increase the voltage of the output.

The voltage modifying device 15 may comprise only the offsetting portion 15a, only the amplifier portion 15b, or both. Alternatively, separate components may be provided to apply the gain and offset, i.e. the portions 15a and 15b may be provided separately as an amplifier and an offset device rather than integrally as shown in FIG. 1. The order in which the gain and the offset are applied to the voltage may be selected by the user, i.e. the amplifier may be provided before the offset device or vice versa.

The resistive state changes of the resistive switching component 20 may be considered as a sequence of resistive state changes which occur over time. For example, a sequence of resistive state changes are depicted by the data values in FIG. 3b. As can be seen, the resistance of the resistive switching component 20 starts at an initial resistance ($R_i$), and generally increases for a predetermined period of time (in this case around 0.5 s) at which point the resistance is reset. It is noted that the resistance may also decrease depending on the polarity of the event and the operating characteristics of the resistive switching component 20 (which are to some extent controllable). As the resistance varies, there are changes of resistive states in response to spikes in the output (which correspond to spikes in the neural waveform indication a neurological event). The sequence of resistive changes may be defined as the successive occurrence of a series of resistive state changes.

The data values may be in various different forms and there may be various different relationships which exist between the resistance of the resistive switching component 20 and the data values. The relationship between the resistance of the resistive switching component 20 and the data values, means that the data value can represent the resistive state changes, and more particularly, can represent the sequence of resistive state changes. Most simply for example, the data values may be proportional to the resistance of the resistive switching component 20. For example, the data values may equate to sampled values of the resistance of the resistive switching component 20 over time.

The data values may be proportional to the resistance of the resistive switching component 20. For example, the data values may be directly proportional to the resistance of the resistive switching component 20. Alternatively, the data values may have a non-linear relationship with the resistance of the resistive switching component 20. For example, the data values may be proportional to the derivative of the resistance with respect to time. The data values may be a function or transform of the resistance of the resistive switching component 20, e.g. using any derivative, integral or averaging operators, etc. In the figures and examples described below, the data values are generally directly proportional to one another. Thus, the figures which show graphs of the resistance could also show the data values representing the resistance. How closely the data values and the resistance correspond would depend on how often the resistance is sampled to obtain the data values.

The method may comprise a step of transforming the resistance of the resistive switching component 20 to arrive at the data values above. For example, a transformation device 30b may be provided. The transformation device 30b may be configured to encode a function or transform of the resistance of the resistive switching component 20 as described above. Such a transformation device 30b is depicted in FIG. 4b. The transformation device 30b is shown as a separate device from the processor 25 and the resistive switching component 20, however, the transformation device 30b could be integral to the processor 25 or the resistive switching component 20.

Figure 4A:
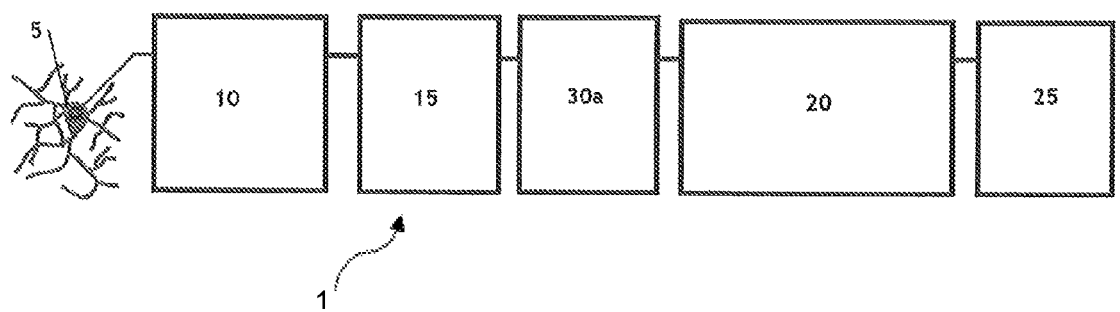
FIGS. 4a and 4b show variations of FIG. 1 further comprising a transformation device.
Figure 4B:
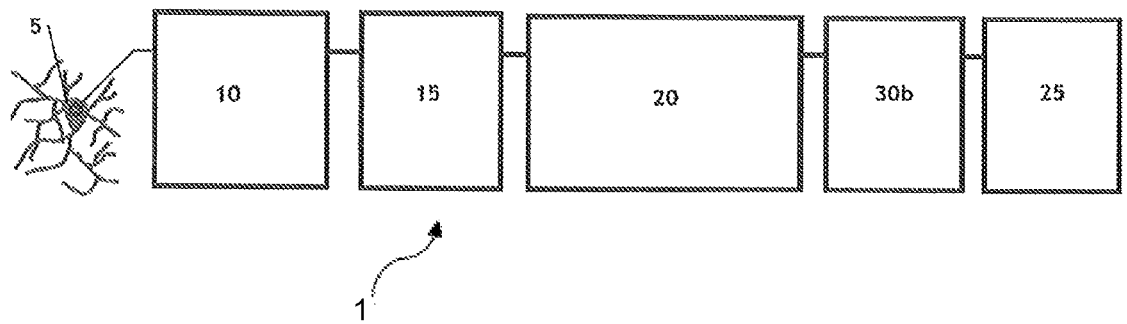

Additionally or alternatively, a transformation device 30a may be provided as depicted in FIG. 4a. The transformation device 30a may be configured to encode a function or transform of the output of the sensor 10 (or the voltage modifying device 15). In other words, the transformation device 30a may apply a function or transform to the voltage before it is applied to the resistive switching component 20. Thus, the output is transformed prior to applying the output to the resistive switching component 20. For example, similarly to the function and transforms described above, the function or transform may use any derivative, integral or averaging operators, etc. The transformation device 30a is shown as a separate device from the processor sensor 10 and resistive switching component 20, however, the transformation device 30a could be integral to the processor 25 or the resistive switching component 20.

The method may further comprise measuring the resistance of the resistive switching component 20 and determining data values representing the resistance of the resistive switching component 20. Data values representing the resistance of the resistive switching component 20 inherently represent the sequence of resistive state changes which are specific variations in the resistance of the resistive switching component 20.

The data values received from the resistive switching component 20 are processed, for example, using a processor 25 as depicted in FIG. 1. The system 1 may be considered as a memristor-based, neural-signal processing platform and/or a memristor-based spike sorting platform. The received data values can be processed to identify a resistive state change corresponding to a neurological event. Information about the neurological event can be obtained, wherein the information is not temporal information. I.e. the information obtained by the processor 25 does not relate to the timing of the neurological event, it relates to another characteristic such as the location of the neurological event. The processing may further comprise obtaining temporal information about the neurological event. However, it is to be understood that this is optional and in addition to the information obtained by the processor 25.

FIG. 3a depicts an exemplary voltage output from the neurological sensor 10, which may optionally have passed through the voltage modifying device 15. As described above, the resistive state of the resistive switching component 20 may vary over time due to the voltage output. The data values may represent the resistance over time and may be the same as the values shown in FIG. 3b. Thus, for example, the data values correlate to the resistance of the resistive switching component 20, thus representing the change of resistive state. As depicted in FIG. 3b, the change in resistance may increase due to the applied voltage over time, thus the resistive switching component 20 may be referred to as an integrating sensor. The data values, as depicted in FIG. 3b, can be processed to determine information relating to the neurological events. The timing of the neurological events is depicted in FIG. 3c which will be seen to correlate to the spikes in the voltage value of the output from the neurological sensor depicted in FIG. 3a.

A resistive state change may be identified by identifying a feature in the received data values. The feature may be a portion of the received data values. The feature comprises a time window of data values in which a change in the data values is greater than a predefined value within a predefined time interval. In other words, the feature indicates a resistive state change, which is when the change in resistance is large enough change within a fixed time period. Examples of identified features are circled in FIG. 3b and labelled a-g. This means that a rate of change of the resistance has to be above a certain value in order to qualify as a resistive state change. This indicates a correlation to the neurological event because the resulting spike in the neural waveform would likely be large enough to cause a spike in the voltage of the output which, when applied to the resistive switching component 20 would result in a resistive state change represented by the data values.

The predefined value of change can be set, for example, based on previous analysis of data values relating to neurological events. Similarly, the predefined time interval can also be set, for example, based on previous analysis of data values relating to neurological events. In this way variation of the neural waveform which relates to a spike (i.e. a neurological event) can be identified as a feature relating to a neurological event. This means that variation in the neural waveform which does not relate to a neurological event would not result in a resistive state change, and would not result in a resistive state change. The method may only process the data values relating to the resistive state changes and variation in other data values may be considered (and optionally ignored) as noise.

Furthermore, not all resistive state changes necessarily correspond to a neurological event. A resistive state change may be deemed to have occurred, but the resistive state change may be too small to relate to a neurological event. Thus, even if the rate of change of the data values is large enough to qualify as a feature, the overall size of the change may be too small and may be deemed to be noise rather than a neurological event. A threshold change value may be determined, and when the size of a change of a feature is below the threshold value, the feature may be considered to be noise.

The threshold change value may be based on results of previous experiments or may be set as a predefined value which can be dynamically changed as results are generated. FIG. 5a depicts a plot wherein the data values have been processed to show a change in resistive state along the x-axis and initial resistive state along the y-axis. Thus, the x-axis correlates to the change in resistance during a resistive state change, i.e. the size of the change of the data values of the feature. FIG. 5a depicts a threshold change value due to the greyed out area on the left of the graph. The threshold change value is depicted in FIG. 5a as approximately 0.3 kΩ. Thus in the example depicted in FIG. 5a, if the size of the change in the data values of the feature is below 0.3 kΩ, then the feature is considered to be noise rather than equating to a neurological event.

As depicted in FIG. 2b, as the resistance increases over time, the resistance of the resistive switching component 20 appears to reach a saturation point. When further voltage is applied to the resistive switching component 20 after the saturation point, there may be little or no change in the resistance of the resistive switching component 20. Additionally, as shown in FIG. 2b, as the resistance increases, the effect that further applied voltage has on the resistance decreases. For the same applied voltage, the change in resistive state may vary depending on the resistance of the resistive switching component 20 when the voltage is applied, e.g. a voltage may cause a smaller change in resistance when the initial resistance is higher. This means that the resistance is less responsive to change due to an applied voltage when the resistive switching component 20 has a higher initial resistance. The same applies asymmetrically for decreases in resistive state.

Thus, it is beneficial to process the data values in a way which accounts for the variation of response of the resistive switching component 20. One way of helping address this issue is to reset the resistance of the resistive switching component 20. As depicted in FIG. 3b, the resistance of the resistive switching component 20 may optionally be reset to an initial value. The method may comprise measuring the resistance when it is determined that a resistive state change has occurred. This is asynchronous measurement which occurs when the resistance changes significantly and a mechanism trips allowing an accurate measurement to be taken. Alternatively, the method may comprise measuring the resistance after a fixed period of time. Thus, the data values may sample the resistance of the resistive switching component 20 at equal intervals of time.

As will be clear from the description above, the change of resistance of the resistive switching component 20 will not be directly proportional to the voltage applied due to the output from the neurological sensor. The data values therefore need to be analysed in view of this.

The method can process the data values in such a way that information can be extracted relating to the neurological events. For example, the data values can be plotted as depicted in FIGS. 5a and 5b. FIG. 5b depicts the information of FIG. 5a. However, because the points in FIG. 5a may not be entirely clear in greyscale, FIG. 5b distinguishes between the points shown in FIG. 5a but only for values relating to a neurological feature, i.e. for values above the threshold change value.

The method comprises a step of processing the data values to identify the resistive state change corresponding to a neurological event. As described above, this may include identifying a feature in the received data values. Characteristic information, e.g. relating to size of change in the data values of the feature and/or a size of a reference data value within the feature as referred to below, quantifying the feature may be determined. Specific characteristics relating to the identified feature may be used to obtain information about the neurological event. For example, the processing may include identifying the size of the change in the data values of the feature, e.g. by comparing the data values at the start and the end of the feature. For example, if the data values directly correspond to the resistance of the resistive switching component 20, as depicted in FIG. 3b, the size of the change would be the change in resistance over time from the start to the end of each of the features identified as a-g.

Additional or alternative characteristics of the feature may be used to obtain information about the neurological event. The processing may include identifying a reference data value within the feature. The reference value may be a data value corresponding to a start of the resistive state change of the feature. The reference value may be a data value corresponding to an end of the resistive state change of the feature. The reference value may be a data value corresponding to a predetermined percentile value of the feature. The reference value may be a data value corresponding to an average value of the feature, e.g. the mean of the data values throughout the feature.

There may be various ways of processing the data values to obtain information. Preferably, analysis can be carried out on the feature based on the characteristic information which is determined. The method comprises obtaining information about the neurological event from the characteristics, such as the size of the change of data values of the feature and/or the size of a reference data value within a feature.

For example, as described in FIGS. 2b and 2e of "Real-time encoding and compression of neuronal spikes by metal-oxide memristors" by Isha Gupta, Alexantrou Serb, Ali Khiat, Ralk Zeitler, Stefano Vassanelli and Themistoklis Prodromakis, Nature Communications (ncomms12805), successive resistive state measurements (between which no external bias has been applied to the device) can be used to estimate background variation in measured resistance. This estimation is made in the absence of external signals and can be used to separate the noise from the spikes in the output. Additionally or alternatively, the method may include comparing the change in measured resistance vs. reference resistance, as in FIG. 5a, and performing clustering on the data values in order to classify the spikes which have been identified in the output. This allows identified spikes in the output to be classified into different categories of spikes as described in relation to FIGS. 5a and 5b below. These procedures are fairly independent of one another in principle and both may be used to calibrate the data values.

Determining the change of the data values in a feature may indicate useful information relating to the neurological event. For example, if the data values are proportional to the resistance of the resistive switching component 20, then the change will be an indication of the change of resistance over the resistive state change. The size of the change will indicate the amplitude of the neurological event, e.g. the size of the spike in the neural waveform. Furthermore, the reference data value may also provide useful information. For example, if the reference data value is at (or near) the start of the feature, this can be used to determine an initial resistance of the resistive switching component 20 when the neurological event takes place. This is useful because as described above, the response of the resistive switching component 20 may depend on the initial resistance at the time of the neurological event. Thus, the processing may determine and use this information.

The characteristic information of each data value may be determined and used in different ways. For example, FIGS. 5a and 5b depict a graph showing the initial resistive state and the changes in resistive state. In an example wherein the data values are directly proportional to the resistance of the resistive switching component 20, the size of the reference data value at a start of the neurological event may be the initial resistance of the resistive switching component, and the size of the change in the data values of the feature may be the change in resistance during the change in resistive state. Thus, these characteristics can be compared as shown in FIGS. 5a and 5b. The comparison of the characteristics means that trends in the data values may be identified. The method may comprise the step of determining which of a plurality of classes the neurological event belongs to. The classes can be determined in such a way as to take account of effects such as the saturation effect on the change of resistance.

Preferably, the information can be processed which may include classification and/or clustering of the data values in some way. Thus, the processing may further comprise determining which of a plurality of classes the information belongs to. The classes may otherwise be referred to as clusters. This can be done in various different ways. FIGS. 5a-5c depict a test for defining the classes which can be used to classify the data values. FIG. 5c depicts a frequency histogram of the amplified spiking events used to test/calibrate the groups. The test is described in further detail in the detailed example below. The test is based on using known spikes in neural waveforms to determine the groups shown. Thus, the information shown in these figures includes the values of the magnitude of the neurological event, which is information relating to the neurological event which the present method is being used to determine.

In FIGS. 5a and 5b, the data values below the threshold change value (in section I) are determined to be noise. The remaining data values can be sorted into classes. As can be seen from the graph, many of the data values are then grouped into at least one class. The method comprises classifying the data values in such a way which allows information relating to the neurological event to be determined, other than temporal information. Once the classes have been determined, for example by way of carrying out a test using spikes with known amplitude corresponding to neurological events, then information relating to further neurological events can be determined depending on which class the data value is in.

The classes may be used to group together data values. Data value information relating to the resistive state changes may be reserved using the resistive switching component 20 which allows information relating to the spike amplitude and duration of a neurological event to be determined.

For example, in FIGS. 5a and 5b, data values relating to different spike amplitudes have been shown in different colours. This is more clearly shown in FIG. 5b which uses different shapes for the range of data values which are determined not to be noise, i.e. the data values relating to a spike in the output form the neurological sensor 10 with a voltage from −1V to −1.5V. The data values are separated into different groups depending on the size of the amplitude of the spike in the output from the neurological sensor 10 (or an equivalent used for testing purposes). As depicted in FIG. 5b, the triangles equate to a spike in the voltage output from the neurological sensor 10 between −1.4V to −1.5V, the circles (above the threshold change value, i.e. on the right hand side of the grey portion on the left) equate to a spike in the voltage output from the neurological sensor between −1.2V to −1.4V, and the crosses equate to a spike in the voltage output from the neurological sensor between −1.0V to −1.2V.

Processing the data as described above allows the data values to be grouped in a useful way. In particular, the data values relating to the spikes in the range of −1.0V to −1.2V are shown in class II, the data values relating to the spikes in the range of −1.2V to −1.4V are shown in class III, and the data values relating to the spikes in the range of −1.4V to −1.5V are shown in class IV. The data values within each of these ranges of voltages may be grouped together. Viewing the data values in terms of certain characteristics (in this case the size of the change of resistance across the resistive state change, and the resistance at or near the start of the resistive state change) may allow this grouping to be carried out. The sections II, III and IV may each represent a class of data values. Data values having similar initial resistances may be in different classes, and similarly, data values having similar changes in resistance may be in different classes. The shape of classes in the graph is substantially skewed. This is due to the saturation of the resistive switching component 20 which means that as the initial resistance increases, a smaller change in resistance is expected. The classes are determined in this way as an example.

When the classes are defined, data values for a neurological event may be processed to determine the class of the neurological event. Therefore, for a neurological event in which the amplitude of the spike in the neural waveform is unknown (contrary to FIGS. 5*a-c*), the data value can be processed and it will be possible to determine which class the neurological event belongs in. If the neurological event belongs in class II, this would mean that the voltage amplitude of the neurological event was between −1.0V and −1.2V. Based on this, the location of the neurological event can be determined. Similarly, a different amplitude and thus a different location can be determined if the data value falls within class III, or class IV. The classes depicted in FIGS. 5*a* and 5*b* are exemplary only and fewer or additional classes may be provided, which may be defined with respect to different characteristics of the data than resistance and changes in resistance as included here.

The classifying may be carried out exclusively on data values for which the reference data value is below a threshold. For example, the reference data value may indicate the initial resistance of the resistive state change. As described above, the resistive switching component 20 can become saturated when the initial resistance is high. Thus, it may be preferable to use data values which are obtained when the resistance of the resistive switching component 20, i.e. using data values with low initial resistance. In this way, a threshold may be used to only include a subset of data values for the classifying which are obtained when the resistive switching component is more sensitive (compared to when the resistive switching component 20 is saturated).

Furthermore, the method may further comprise obtaining temporal information about a timing of the neurological event. As described above, the temporal information may relate to the neurological event in a variety of different ways. For example, the temporal information may relate to the time at which the event occurs, this might be a time at which or near when the event starts and/or ends, the temporal information may include the duration of the neurological event, the temporal information may include the average (e.g. the mean) frequency of the neurological events within a fixed interval of time. There may be some synergy between the temporal information and the other information determined because in biology it is known that each individual neuron can only fire up a certain maximum frequency. If two spikes are identified as belonging to the same category occur impossibly close to one another, then the temporal information may affect how the non-temporal information is interpreted. For example, two spikes in the output which are impossibly close together may indicate the existence of at least two neurons firing spikes (rather than one) that have a very similar effects on the sensor/processing method.

The present embodiment may provide a system 1 configured to carry out a method as described above including any of the optional/preferable features. For example, the present embodiment may provide a system 1 for processing data from a neurological sensor comprising a processor 25 configured to receive data values representing a sequence of resistive state changes of a resistive switching component 20 resulting from applying the output from at least one neurological sensor 10 to the resistive switching component 20, wherein the resistive switching component 20 is capable of undergoing a resistive state change when a voltage above a threshold voltage is applied across the resistive component, and wherein the processor is configured to process the received data to identify a resistive state change corresponding to a neurological event and to obtain information about the neurological event other than temporal information from the resistive state change. The system 1 may be the same as the system 1 described above and as depicted in FIG. 1. The processor 25 may therefore receive data values from the neurological sensor 10.

The system 1 may further comprise the resistive switching component 20 configured to receive a voltage and undergo a resistive state change when a voltage above a threshold voltage is applied across the resistive switching component 20. The resistive switching component 20 may be configured to retain a change in resistance caused by the received voltage after the received voltage is removed. In other words, the resistive switching component 20 may retain a history of the voltage applied to the resistive switching component 20. This may only be retained for a short period of time, for example, as described above. If the resistance is retained for a longer period of time, this means that the change in resistance does not necessarily need to be measured at a high frequency to track all the changes of resistance of the resistive switching component 20. No matter the length of time for which the resistance is retained, such a device allows the change of resistance over time to be determined and processed to obtain information about the neurological event.

Additionally or alternatively, the system 1 may further comprise at least one neurological sensor 10 configured to measure a neurological event and to output a voltage relating to the neurological event. The neurological sensor 10 may measures biological signals, e.g. neurological signals, using electrodes, possibly micro-electrodes. Thus the neurological sensor 10 may comprise at least electrodes which can be used in different ways, for example, in vivo or in vitro. Multiple neurological sensors may be used, and may optionally be provided as part of an array. The neurological sensor 10 may be a complementary metal-oxide-semiconductor (CMOS), and may be part of a CMOS multi-electrode-array (MEA).

The neurological sensor 10 may store data relating to the voltage which may be passed to the resistive switching component 20 at a later date, or the neurological sensor 10 may pass the data to the resistive switching component 20 in real time. Either way, the system 1 may optionally comprise an voltage modifying device 15 in order to increase the gain and/or offset of the voltage applied to the resistive switching component 20 as described above. The system 1 may comprise separate components to increase the gain and/or offset, e.g. an amplifier 15*a* and/or an offset device 15*b* as described above.

The system may comprise a transformation device such as 30*a*, configured to transform the output from the neurological sensor 10 prior to the output being applied to the resistive switching component 20 as described above. Additionally or alternatively, the system may comprise a transformation device such as 30*b*, configured to transform the resistance of the resistive switching component 20 as described above.

The system 1 may be a computer-implemented system 1. Thus, the computer implemented system 1 comprises at least one electrical computing device. The processor 25 may be such an electrical computing device. The electrical computing device may be any appropriate device such as a desktop computer, a laptop, a mobile device such as a phone, a tablet etc. The processor 25 may be part of a larger computer system with the ability to process large amounts of data due to the large amount of data generated in the present system 1. The processor 25 may include software, hardware and/or firmware to implement the methods described above. Additionally or alternatively, the processor 25 may include using an integrated circuit and/or a printed circuit board and/or any other appropriate electronic circuit structure.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. It is explicitly stated that all value ranges or indications of groups of entities disclose every possible intermediate value or intermediate entity for the purpose of original disclosure as well as for the purpose of restricting the claimed invention, in particular as limits of value ranges.

DETAILED EXAMPLE

The described embodiments provide a new approach for processing data values to obtain information relating to neurological events by performing spike-sorting through a memristor-based, neural-signal processing platform. It has previously been shown that the inherent threshold property of the memristor, i.e. resistive switching device 20 allows spike-detection through non-volatile resistive state transition. In other words, neurological events can be detected using a non-volatile type of resistive switching device 20. Here, a test memristive device is subjected to a neural recording, i.e. the output from a neurological sensor 10 described above, and the periodically recorded resistive state changes are mapped to the amplitude of the spiking events, wherein the spiking events are neurological events represented by features in the data values. It is found that the resistive state changes can be differentiated into clusters (i.e. classes), where each cluster can be mapped to a range of spiking events in the input neural waveform (which is the input to the neurological sensor 10), thus indicating the address of source neuron.

I. MATERIALS AND METHODS

Exemplary employed devices, concepts and implementation of the MIS system is described below.
A. Memristive Integrating Sensor (MIS) Platform The concept schematic of the proposed MIS platform is illustrated in FIG. 1 and in further detail in FIG. 6. FIG. 1 has been described above. FIG. 6 depicts a schematic for the operation of memristive devices as neural spike integrators. Extracellular neural recordings (i.e. the output from a neurological sensor) are obtained from dissected retinal ganglion cells (which are a particular type of neuron) placed atop CMOS multi-electrode-array (MEA). Voltage-time traces in hundred's of mV range can be stored on to a computing device, such as a PC. (i) Neural data (i.e. the output of the neurological sensor 10) is then processed, optionally with suitable gain and offset settings such that only most significant neural spikes with large amplitude are above the threshold of the device (i.e. the resistive switching component 20). (ii) The memristive devices (i.e. the resistive switching component 20) may be biased with pre-processed neural recordings and the resistive state of the device is assessed periodically. (iii) Significant resistive state changes are separated from insignificant resistive state changes. Modified from [11].

In this example, the retinal neuronal activity is pre-recorded in-vitro from an external CMOS-based platform [14]. The external CMOS based platform corresponds to the neurological sensor 15 indicated above. The acquired waveforms which are the output voltages from the neurological sensor 10 may then be suitably conditioned using key operational parameters e.g. gain (G) and offset (Voff) before feeding it to the memristive devices as depicted in FIG. 6 and marked as section [i]. The appropriately amplified neural signals (which correspond to the output from the neurological sensor 10 described above) are fed to the robust MIS devices using a customised hardware infrastructure [15] in real-time at a sampling rate of 12.2 kHz such that large amplitude neural signals are above the 'inherent threshold' (Vth−) of the device. The MIS device corresponds to the resistive switching component 20 described above. The neural recording is fed to the devices and the resistive state of the device is assessed periodically which occurs in the MIS implementation step marked [ii] in FIG. 6. Optionally, a 'standard schematic' is followed, where the neural recording containing ≈63 kS data-points is fed to the devices in batches of thousand and per batch the resistive state of the DUT is assessed five times offering a compression factor of 200. The same scheme outputs 316 distinct time bins containing the measured resistive state measurements. Finally, the off-line analysis of resistive state changes in each bin differentiates significant resistive state changes from insignificant resistive state changes thus giving an estimation of the spikes detected by the MIS platform as indicated in [iii] of FIG. 6. This describes the processing carried out to determine resistive state changes and to determine which resistive state changes are too small and are considered to be noise as described above.

B. Devices and Electrical Characterisation

Various different devices can be used as a resistive switching component. For example, experiments were carried out using solid-state TiOx devices with a vertical stack structure of Ti/Pt/TiOx/Pt (5/10/25/10 nm) fabricated on Si/SiO2 substrate were utilised. The devices were fabricated according to the following flowchart; 200 nm of insulating SiO2 was thermally grown on 6-inch Silicon wafer. Then three main patterning steps were processed, each contains optical lithography, film deposition and lift-off process. In the first step, 5 nm Titanium (Ti) and 10 nm Platinum (Pt) films were deposited via electron-gun evaporation technology to serve as bottom electrodes, Ti was used for adhesion purposes. In the second, magnetron reactive sputtering system was used to deposit the TiO2-x (x=0.06) active core from Ti metal target. Two plasma sources were used to ensure homogeneous near stoichiometric film. 25 nm thick TiOx was deposited. In the final step, 10 nm Pt top electrodes were deposited using electron-gun evaporation system. At the end of processing, the wafer was diced into 9×9 mm2 chips, which were then wire-bonded in standard packages for measurements and 60×60 µm2 devices were used for the experiments. It will be understood that this is an example of the way in which a resistive switching component could be formed, but other variations are also envisaged.

In this example, the first step in the electrical characterisation methodology is the 'electroforming' of the device-under-test (DUT) (i.e. resistive switching components). Before use, all the devices may be electroformed by employing a ramp of positive voltages (forming voltage of the devices is ≈+6.5V). Next, a 100 µs pulse-based stimulation protocol is used to switch the resistive state of the DUT in both the polarities [16]. For these devices, with negative (positive) polarity the devices switch to high (low) resistive state. Notably, all the devices may possess a Vth– (thresholded-voltage integral, which may otherwise be referred to as a threshold value) above which gradual, non-volatile resistive state changes are obtained and below which no changes in the resistive state of the device are observed. This is described above in relation to FIG. 2. The range of Vth– of TiOx devices in the present example is ±0.6-2.2V and slightly asymmetric voltages are typical of this device family.

Figure 2:
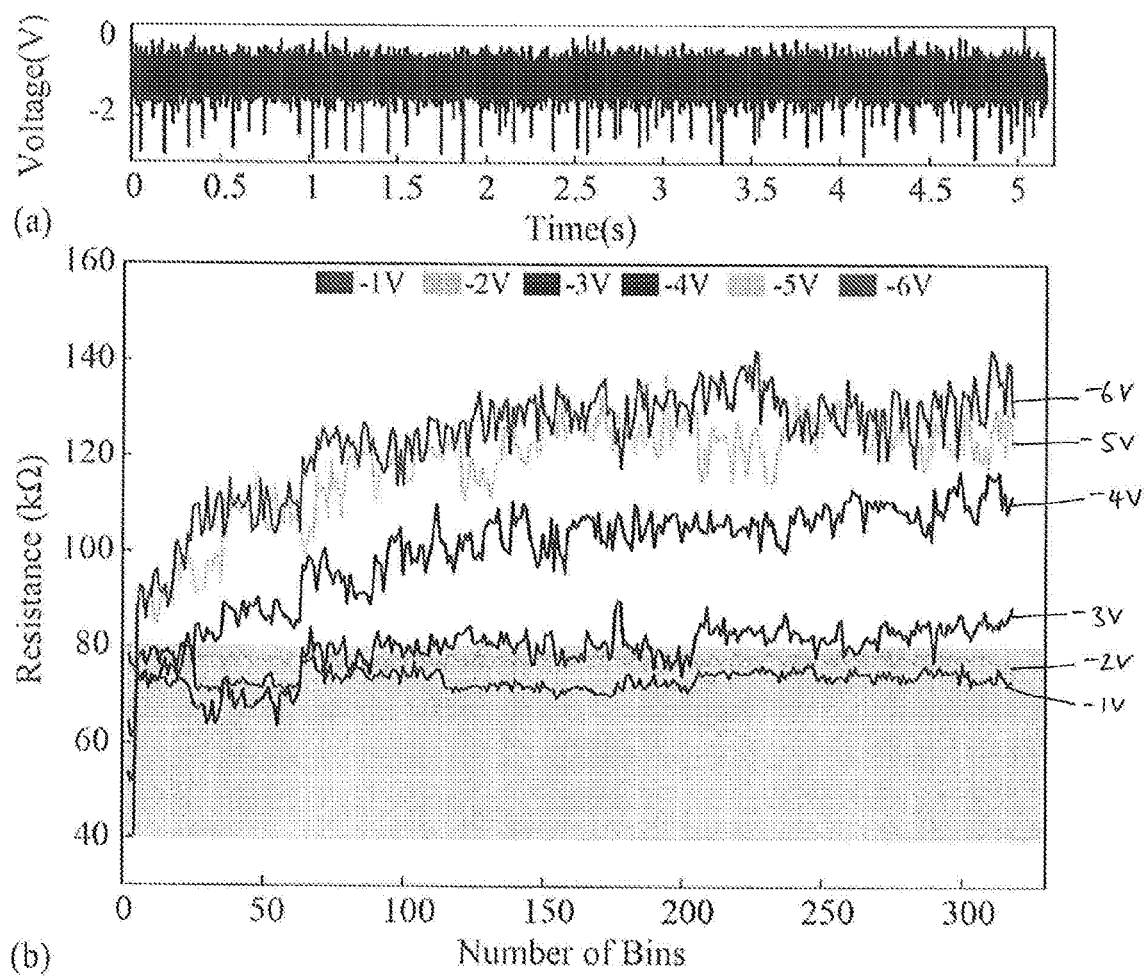

For this study, a reference neural waveform (voltage-time series) was amplified from –1V to –6V in steps of 1V, as illustrated in FIG. 2a. In FIG. 2 a DUT subjected to a reference neural recording amplified with voltages from –1V to –6V in steps of 1V. (a) The reference neural recording used for this experiment with significant events in the negative polarity. (b) The resistive state output of the device as captured by the MIS platform after every round of experiment. Notably, in this case, with negative (positive) polarity there is an overall increase (decrease) in the resistive state of the device. The grey band indicates the initial resistive state range ($R_i$).

The resulting resistive state of the target device in response to the biased neural recording as captured by the MIS platform is illustrated in FIG. 2b. The DUT was manually reset to an initial resistive state ($R_i$) after every round of experiments using a positive polarity pulse lasting for 100 µs ($R_i$ range being 40-80k). No resistive state change can be observed for lower voltages i.e. –1V and –2V ('sub-threshold' region) whilst distinct resistive state changes can be observed for higher voltages i.e. –3V--6V ('supra-threshold' region); –3V being the Vth– of the DUT. A similar experiment was performed for the events in the opposite polarity, with the Vth+ of the device being +3V. The 'sub-threshold' region promotes the filtering of noise whereas the 'supra-threshold' helps in spike-detection (extrapolated from the significant resistive state changes in each bin). These results firmly establish the fact that the output of the MIS devices (i.e. the data values from the resistive switching component 20) is sensitive to: a) amplitude, and b) polarity of the input signal. Moreover, since the output of memristive device is function of integral of input voltage, the resistive state changes in principal could be mapped to the spike-strength.

Furthermore, FIG. 2 unveils a second important observation. The continuous operation of the device for a specific amplitude leads to saturation of the resistive state of the DUT; failing to detect any further significant activity in the input waveform For instance at –4V, the resistive state of the device continuously increases from 80kΩ to 100kΩ for ≈100 bins, following which the DUT saturates. One step further increase in the voltage (–5V) causes the device to saturate at a higher resistive state of ≈130k, however, an additional increase of voltage (i.e. –6V) infers no change in the resistive state of the DUT. This crucial observation suggests two important things: (a) as the device reaches its operational ceiling (high resistive state), the device needs to be 'reset' to its initial state in order to obtain continuous changes in the resistive state and thus avoid saturation, and (b) to map the resistive state changes to distinct neural events with specific amplitude the initial resistive state ($R_i$) of the DUT must be in an appropriately smaller range and should not drift considerably. Notably, the large amplitude Vth– obtained in this experiment are countered by using optimised TiOx devices for successive experiments.

II. DATA PROCESSING AND RESULTS

Figure 3:
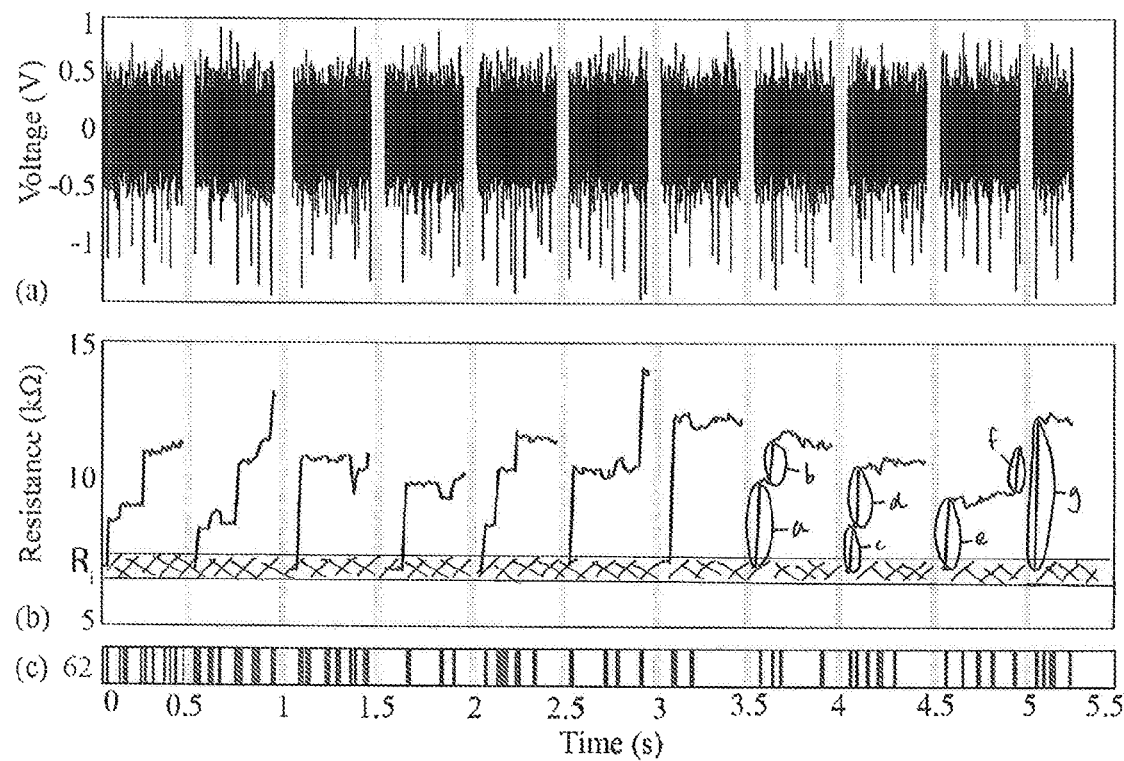
FIG. 3a depicts an output from a sensor, wherein the output has a voltage which varies over time, and which is separated into distinct periods of time.
FIG. 3b depicts values representing the change in the resistance of a resistive switching component when the voltage of FIG. 3a is applied across it.
FIG. 3c depicts the events in each distinct period of time.

Results available from the above described test and data analysis is described below The practical limitation in operation of MIS elements as 'spike-detectors' is the saturation of the resistive state of the DUT. One strategy to combat this issue and ensure the operation of the device in its functional regime is to introduce 'regular resets', as demonstrated in FIG. 3. For this experiment, the same neural recording with 63 kS as illustrated in FIG. 3a was sliced in eleven subsets. Each sub-neural recording lasted for approximately 0.5 s and contained 6k data points. The gain and offset parameters for this specific experiment was fixed at 2.2 and 0, respectively. The resistive state time-evolution of the target device in response to the biased sub-neural recordings is shown in FIG. 3b, separated by grey bands. The DUT was manually initialised to an ($R_i$) of ≈6-8k after feeding each subset of neural data, represented by hatched band in FIG. 3b. In our previous work, we have analysed the normalised resistive state changes in each bin and estimated the spike-count for each recording slice as presented in FIG. 3c.

FIG. 3 depicts manual frequent resets in the initial resistive state ($R_i$) of the device upon saturation. (a) Slicing of a neural recording (i.e. output from a neurological sensor 10) in eleven parts. Each sub-neural recording lasts approximately 0.5 s separated by grey bands. (b) Transient response of the DUT in response to the biased sub neural recording with gain=0.2 and offset=0. (c) The number of spikes detected corresponding to each slice. The hatched band indicates the range of the initial resistive state ($R_i$) which falls in the range of 6-8 k.

Moving on, the resistive state changes are sensitive to both amplitude and polarity of the input neural signal. Therefore, the information on spike amplitude/duration is preserved in the magnitude of the resistive state modulation to a certain extent, which can be used to locate the address of source event in the biased neural waveform. To examine this hypothesis, the data obtained from FIG. 3 is analysed in a different facet from the objective of mapping the resistive state changes to the corresponding spike amplitude. Since the initial resistive state ($R_i$) for all the sub-neural recordings is in relatively smaller range, the resistive state changes ($\Delta R$) are now plotted as a function of initial resistive state (RO) in each bin, as illustrated in FIGS. 5a and 5b. These super-imposed scatter plots are analysed in reference to the maximum assigned amplitude of the neural (spiking) event in each bin. FIG. 5c represents the frequency distribution of the maximum spike amplitude values obtained from all the bins.

FIG. 5. Towards spike sorting. (a and b) Scatter plots for the initial resistive state (Ro) vs changes in resistive state ($\Delta R$) in each bin for every sub-neural recording employed in FIG. 5. '*' symbol denotes the outlier event in the group, [−1.2V−−1.0V] (c) Frequency histogram for the amplified spiking events used for this experiment.

To sort the resistive state changes with respect to the spike-amplitude, the entire range of the spike-amplitude is divided into smaller groups. For this recording, the obtained range is (−1.5V-1V) as seen in FIG. 5c, which is further sub-divided into six groups, as summarised in Table. I. All the resistive state changes in FIGS. 5a and 5b are analysed in reference to the assumed six groups of spike-amplitude. The choice of the first group was done on the basis that throughout the experimental measurements, the Vth− of the TiOx devices is found to be greater than ±0.6V, hence the 'sub-threshold region' was assumed as one group. As for the remaining groups, the range is divided in intervals of 0.2V, to introduce no experimental bias. In addition, Table.I indicates the maximum and minimum amplitude of the spiking-events present in each sub-group.

TABLE I

DISTRIBUTION OF THE RANGE OF THE AMPLITUDE OF SPIKING EVENTS IN SUB-GROUPS. MAXIMUM AND MINIMUM VALUE OF SPIKING EVENTS IN EACH SUB-GROUP IS ALSO INDICATED.

| Bins | Max. Voltage (V) | Min. Voltage |
|---|---|---|
| [−0.6 V, 1 V) | 0.9084 | −0.5840 |
| [−0.8 V, −0.6 V) | −0.6164 | −0.7786 |
| [−1.0 V, −0.8 V) | −0.8110 | −0.9733 |
| [−1.2 V, −1.0 V) | −1.0057 | −1.1679 |
| [−1.4 V, −1.2 V) | −1.2003 | −1.395 |
| [−1.5 V, −1.4 V) | −1.4274 | −1.4599 |

The first second and third group i.e. [−0.6V, +1V), [−0.8V, −0.6V) and [−1.0V, −0.8V), mostly constitutes of 'noise' and doesn't affect the resistive state of the device. Clearly, most of the resistive state changes are centred around zero and fall under the 'sub-threshold' region of the device. These resistive state changes indicate the first cluster presented in FIGS. 5a and b, marked in grey (I). For the fourth sub-group i.e. [−1.2V, −1.0V), a $\Delta R$ of up to ≈2kΩ is noted. Importantly, an event present in the beginning of the recording will lead to a stronger overall change in the resistive state of the device in comparison to the same event present in the latter part of the recording. This observation is in line with the saturation behaviour of the resistive state of the MIS devices obtained for different amplitudes, as explained in FIG. 2b. This explains the smaller change in resistive state with events with higher RO (for instance at ≈8-9k). Therefore, these resistive state changes can be grouped in one cluster.

From the same fourth group, the resistive state change marked by asterisk symbol ('*'), as shown in FIGS. 5a and 5b is an outlier and can be explained. This specific point belongs to the third sub-neural recording in FIG. 3a, containing a strong positive polarity event which leads to a resistive state drop. However, in the operation of MIS platform, the resistive state measurements are assigned to the max. amplitude event in each bin. Therefore, this resistive state change has been assigned to the higher negative polarity event i.e. −1.1V, present in the same bin, preceding the positive polarity event although the change in the state happens due to the positive polarity event.

Similarly, for the fifth group containing stronger amplitude d events i.e. [−1.4V,−1.2V), a higher $\Delta R$ of up to 4kΩ is obtained which points to the III cluster. Finally, for the last group i.e. [−1.5V,−1.4V), the IV cluster is obtained where $\Delta R$ changes are similar to the III cluster. This can again be explained by the fact that the spiking events are present in the latter part of the recording, which can be understood by a higher initial resistive state i.e. Ro (as illustrated), in turn causing relatively smaller changes in resistive state.

The three distinct clusters containing significant resistive state changes (clusters II, III and IV) signifies the presence of at least three distinct spikes in the considered groups for spike amplitude.

III. DISCUSSION

A discussion of the results and data analysis is included below

The presented results in the manuscript is our preliminary approach to decipher the structure present in the resistive state changes in relation to the spike amplitude. Importantly, these results are entirely based on the assumption that by following this methodology, a) spikes with similar amplitude cannot be distinguished, and b) the initial resistive state ($R_i$) of the employed device should be approximately in a similar range i.e. should not drift drastically. The analysis of the resistive state changes with even smaller ranges of spike amplitude and modelling of the clusters, which can be thought of as lines remains as the future work. The major significance of this work lies in the fact that our previous work limited the operation of MIS platform with 'spike-detection' function only, however, the presented approach is our first insight towards 'spike-sorting' capability from the same platform, given the mentioned assumptions.

IV. CONCLUSION OF TEST EXAMPLE

The above test and analysis presents the first approach for mapping the memory state changes of the recently proposed, 'memristive integrating sensor' to the spiking events in the original neural waveform. The resetting operation saves the memristive device from undergoing saturation and permits continuous detection of spikes in the biased neural waveform. The obtained resistive state transitions are then studied in reference to the spike amplitude segregated in different groups. Clusters of resistive state changes can be differentiated in response to the assumed groups of spike amplitudes, thus confirming the potential of MIS platform for 'spike-sorting.'

REFERENCES

[1] U. Frey et al., "Microelectronic system for high-resolution mapping of extracellular electric fields applied to brain slices. Biosensors & bioelectronics, vol. 24, no. 7, pp. 2191-8, Mar. 2009.

[2] A. Hierlemann et al., "Growing Cells Atop Microelectronic Chips: Interfacing Electrogenic Cells In Vitro With CMOS-Based Microelectrode Arrays," Proceedings of the IEEE, vol. 99, no. 2, pp. 252-284, February 2011.

[3] C. M. Lopez et al., "22.7 A 966-electrode neural probe with 384 configurable channel si n0.13 mSO ICMOS, 2016 IEEE International Solid-State Circuits Conference (ISSCC), pp. 392-393, 2016. [Online]. Available:

[4] S. E. Paraskevopoulou et al., "A sub-luW neural spike-peak detection and spike-count rate encoding circuit," in2011 IEEEBiomedicalCircuits and Systems Conference (BioCAS). IEEE, November 2011, pp. 29-32.

[5] G. Baranauskas, "What limits the performance of current invasive brain machine interfaces?" Frontiers in systems neuroscience, vol. 8, no. April, p. 68, January 2014.

[6] H. G. Rey et al., "Past, present and future of spike sorting techniques." Brain research bulletin, vol. 119, pp. 106-117, Apr. 2015.

[7] A. H. Marblestone et al., "Physical principles for scalable neural recording" Frontiers in comp. neuroscience, vol. 7, p. 137, Jan. 2013.

[8] M. S. Lewicki, "A review of methods for spike sorting: the detection and classification of neural action potential classification of neural action potentials," Network: Computation in Neural systems, vol. 9.4, no. January, pp. R53-R78, 1998.

[9] L. F. Nicolas-Alonso et al., "Brain computer interfaces, a review." Sensors (Basel, Switzerland), vol. 12, no. 2, pp. 1211-79, Jan. 2012.

[10] E. N. Brown et al., "Multiple neural spike train data analysis: state-of-the-art and future challenges." Nature neuroscience, vol. 7, no. 5, pp. 456-61, May 2004.

[11] I. Gupta et al., "Memristive integrative sensors for neuronal activity," arXiv preprint arXiv:1507.06832, 2015.

[12] D. S. Jeong et al., "Emerging memories: resistive switching mechanisms and current status," Reports on Progress in Physics, vol. 75, no. 7, p. 076502, July 2012.

[13] T. Prodromakis et al., "Two centuries of memristors." Nature materials, vol. 11, no. 6, pp. 478-81, June 2012.

[14] B. Eversmann et al., "A 128×128 CMOS Biosensor Array for Extracellular Recording of Neural Activity," IEEE Journal of Solid-State Circuits, vol. 38, no. 12, pp. 2306-2317, 2003.

[15] A. Serb et al., "Live demonstration: A versatile, low-cost platform for testing large ReRAM cross-bar arrays." IEEE International Symposium on Circuits and Systems, vol. 9, no. 5, p. 4799, 2014.

[16] I. Gupta et al., "A Cell Classifier for RRA M Process Development, IEEE Transactions on Circuits and Systems II: Express Briefs, vol. 62, no. 7, pp. 676-680, 2015.

The invention claimed is:

1. A method for processing a signal from at least one sensor configured to convert a physical phenomenon to an output signal that can be measured to detect an event, comprising:
applying the output signal to a resistive switching component, optionally wherein the output signal is transformed prior to applying the output signal to the resistive switching component;
receiving data values representing a sequence of resistive state changes of the resistive switching component resulting from applying the output signal to the resistive switching component, wherein the resistive switching component is capable of undergoing a non-volatile resistive state change when a voltage above a threshold voltage is applied across the resistive switching component, wherein the resistive switching component is configured to change its resistive state as a function of the integral of the voltage; and
processing the received data values to identify a resistive state change corresponding to the event, thereby detecting the event, and to obtain information about the event other than temporal information from the resistive state change; and
wherein the data values have a non-linear relationship with a resistance of the resistive switching component.

2. The method of claim 1, wherein the identifying of a resistive state change corresponding to an event comprises identifying a feature in the received data values, the feature comprising a time window of data values in which a change in the data values between any two data points in a predetermined time interval is greater than a predefined value, wherein the feature indicates a resistive state change, which is when the change in resistance is a large enough change within a fixed time period.

3. The method of claim 2, wherein the processing comprises obtaining information about the event from a size of the change in the data values of the feature.

4. The method of claim 2, wherein the processing comprises obtaining information about an event from both 1) a size of the change in the data values of the feature; and 2) a size of a reference data value within the feature, wherein the reference data value comprises one of the following: a data value corresponding to a start of the resistive state change of the feature; a data value corresponding to an end of the resistive state change of the feature; a data value corresponding to a predetermined percentile value of the feature or to an average value of the feature.

5. The method of claim 4, wherein the processing further comprises determining which of a plurality of classes the event belongs to.

6. The method of claim 5, wherein classifying is carried out exclusively on data values for which the reference data value is below a threshold.

7. The method of claim 1, wherein the processing further comprises obtaining temporal information of the event.

8. The method of claim 1, wherein the data values are obtained by sampling a resistance of the resistive switching component at equal intervals.

9. The method of claim 1, wherein the data values are proportional to a derivative of the resistance with respect to time.

10. The method of claim 1, wherein the output is transformed prior to applying the output to the resistive switching component.

11. The method of claim 1, wherein the event is a neurological event.

12. The method of claim 1, wherein the resistive switching component is configured to change its resistive state as a function of a weighted integral of the voltage.

13. A system for processing a signal from at least one sensor configured to convert a physical phenomenon to an output voltage signal that can be measured to detect an event, the system comprising:
a resistive switching component configured to receive the output signal from the at least one sensor and to undergo a non-volatile resistive state change when a voltage above a threshold voltage is applied across the resistive switching component, optionally wherein the output signal is transformed prior to applying the output signal to the resistive switching component, and wherein the resistive switching component is configured to change its resistive state as a function of an integral of the voltage; and
a processor configured to:
receive data values representing a sequence of resistive state changes of the resistive switching component resulting from applying the output from the at least one sensor to the resistive switching component; and
process the received data to identify a resistive state change corresponding to the event, thereby detecting the event, and to obtain information about the event other than temporal information from the resistive state change; and wherein the data values have a non-linear relationship with a resistance of the resistive switching component.

14. The system of claim 13, wherein the event is a neurological event.

15. The system of claim 13, wherein the at least one sensor is further configured to measure the event and to output a voltage relating to the event.

16. The system of claim 15, wherein the event is a neurological event and the at least one sensor is a neurological sensor.

17. The system of claim 13, wherein the resistive switching component is configured to change its resistive state as a function of a weighted integral of the voltage.

18. A method for processing data from at least one sensor configured to measure an event, comprising:
applying an output relating to the event from the at least one sensor to a resistive switching component, optionally wherein the output is transformed prior to applying the output to the resistive switching component,
receiving data values representing a sequence of resistive state changes of a resistive switching component resulting from applying the output from the at least one sensor to the resistive switching component, wherein the resistive switching component is capable of undergoing a non-volatile resistive state change when a voltage above a threshold voltage is applied across the resistive switching component, wherein the resistive switching component is configured to change its resistive state as a function of an integral of the voltage; and
processing the received data values to identify a resistive state change corresponding to the event and to obtain information about the event other than temporal information from the resistive state change,
wherein the identifying of a resistive state change corresponding to an event comprises identifying a feature in the received data values, the feature comprising a time window of data values in which a change in the data values between any two data points in a predetermined time interval is greater than a predefined value, wherein the feature indicates a resistive state change, which is when the change in resistance is a large enough change within a fixed time period,
wherein the processing comprises obtaining information about an event from both 1) a size of the change in the data values of the feature; and 2) a size of a reference data value within the feature, wherein the reference data value comprises one of the following: a data value corresponding to a start of the resistive state change of the feature; a data value corresponding to an end of the resistive state change of the feature; a data value corresponding to a predetermined percentile value of the feature or to an average value of the feature,
wherein the processing further comprises determining which of a plurality of classes the event belongs to, and
wherein classifying is carried out exclusively on data values for which the reference data value is below a threshold.

19. The method of claim 18, wherein the processing comprises obtaining information about the event from a size of the change in the data values of the feature.

20. The method of claim 18, wherein the processing further comprises obtaining temporal information of the event.

21. The method of claim 18, wherein the data values are obtained by sampling a resistance of the resistive switching component at equal intervals.

22. The method of claim 18, wherein the data values are proportional to a resistance of the resistive switching component.

23. The method of claim 18, wherein the data values have a non-linear relationship with a resistance of the resistive switching component.

24. The method of claim 23, wherein the data values are proportional to a derivative of the resistance with respect to time.

25. The method of claim 18, wherein the output is transformed prior to applying the output to the resistive switching component.

26. The method of claim 18, wherein the event is a neurological event.

27. The method of claim 18, wherein the resistive switching component is configured to change its resistive state as a function of a weighted integral of the voltage.

28. A system for processing data from at least one sensor configured to measure an event, the system comprising
a resistive switching component configured to receive an output relating to the event from the at least one sensor and to undergo a non-volatile resistive state change when a voltage above a threshold voltage is applied across the resistive switching component, optionally wherein the output is transformed prior to applying the output to the resistive switching component, and wherein the resistive switching component is configured to change its resistive state as a function of an integral of the voltage; and
a processor configured to:
receive data values representing a sequence of resistive state changes of the resistive switching component resulting from applying the output from the at least one sensor to the resistive switching component; and
process the received data to identify a resistive state change corresponding to the event and to obtain information about the event other than temporal information from the resistive state change,
wherein the identifying of a resistive state change corresponding to an event comprises identifying a feature in the received data values, the feature comprising a time window of data values in which a change in the data values between any two data points in a predetermined time interval is greater than a predefined value, wherein the feature indicates a resistive state change, which is when the change in resistance is a large enough change within a fixed time period,
wherein the processing comprises obtaining information about an event from both 1) a size of the change in the data values of the feature; and 2) a size of a reference data value within the feature, wherein the reference data value comprises one of the following: a data value corresponding to a start of the resistive state change of the feature; a data value corresponding to an end of the resistive state change of the feature; a data value corresponding to a predetermined percentile value of the feature or to an average value of the feature,
wherein the processing further comprises determining which of a plurality of classes the event belongs to, and
wherein classifying is carried out exclusively on data values for which the reference data value is below a threshold.

29. The system of claim 28, wherein the event is a neurological event.

30. The system of claim 28, wherein the at least one sensor is further configured to measure the event and to output a voltage relating to the event.

31. The system of claim 30, wherein the event is a neurological event and the at least one sensor is a neurological sensor.

32. The system of claim 28, wherein the resistive switching component is configured to change its resistive state as a function of a weighted integral of the voltage.

* * * * *